United States Patent [19]
Ketcham et al.

[11] Patent Number: 6,033,663
[45] Date of Patent: *Mar. 7, 2000

[54] NUCLEIC ACIDS ENCODING GDP-FUCOSE PYROPHOSPHORYLASE

[75] Inventors: Catherine M. Ketcham, Encinitas, Calif.; Alan D. Elbein, Little Rock, Ark.; Richard R. Drake, Little Rock, Ark.; Irena Pastuszak, Little Rock, Ark.

[73] Assignee: Neose Technologies, Inc., Horsham, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/826,964

[22] Filed: Apr. 9, 1997

Related U.S. Application Data

[60] Provisional application No. 60/015,241, Apr. 10, 1996.

[51] Int. Cl.$^7$ ............................. A61K 38/51; C12N 9/12; C07H 21/04; C07K 1/00

[52] U.S. Cl. ...................... 424/94.5; 435/194; 435/69.1; 435/252.3; 435/320.1; 536/23.2; 530/350

[58] Field of Search ................... 424/94.5; 435/194, 435/69.1, 252.3, 320.1; 536/23.2; 530/350

[56] References Cited

U.S. PATENT DOCUMENTS

| | | | |
|---|---|---|---|
| 5,079,353 | 1/1992 | Ratcliffe et al. | 536/53 |
| 5,164,374 | 11/1992 | Rademacher et al. | 514/23 |
| 5,278,299 | 1/1994 | Wong et al. | 536/53 |
| 5,288,637 | 2/1994 | Roth | 435/288 |
| 5,296,594 | 3/1994 | Ratcliffe et al. | 536/53 |
| 5,324,663 | 6/1994 | Lowe | 435/320.1 |
| 5,344,870 | 9/1994 | Ratcliffe et al. | 525/54.2 |
| 5,352,670 | 10/1994 | Venot | 514/54 |
| 5,374,541 | 12/1994 | Wong et al. | 435/74 |
| 5,374,655 | 12/1994 | Kashem et al. | 514/54 |
| 5,428,025 | 6/1995 | Brandley et al. | 514/55 |

FOREIGN PATENT DOCUMENTS

| | | |
|---|---|---|
| 622 73919 | 11/1987 | European Pat. Off. . |
| 0 319 253 | 6/1989 | European Pat. Off. . |
| WO 90/13300 | 11/1990 | WIPO . |
| WO 91/19502 | 12/1991 | WIPO . |
| WO 92/07572 | 5/1992 | WIPO . |
| WO 92/16640 | 10/1992 | WIPO . |
| WO 94/25614 | 10/1994 | WIPO . |
| WO 94/25615 | 11/1994 | WIPO . |
| WO 94/26760 | 11/1994 | WIPO . |
| WO 96/32491 | 10/1996 | WIPO . |
| WO 96/32492 | 10/1996 | WIPO . |

OTHER PUBLICATIONS

Stiller et al. Liebig Ann. Chem. 1992, 467–471.
Janson, J–C. Trends in Biotechnology. 2(2): 31–38, 1984.
1990 Sigma Chemical Company Catalogue, pp. 217, 461, 729.
Auge, et al. (1990). Carbohydrate Research 200:257–268.
Auge, et al. (1986). Carbohydrate Research 151:147–156.
Berg, Ellen L., et al. (1991). "A Carbohydrate Domain Common to Both Sialyl Le(a) and Sialyl (x) is Recognized by the Endothelial Cell Leukocyte Adhesion Molecule ELAM–1." J. Biol. Chem., 266(23):14869–14872.
Brandley, Brian K., et al. (1990). "Carbohydrate Ligands of the LEC Cell Adhesion Molecules." Cell, 63:861–863.
Burczak, J.D. et al. (1984). "Characterization of a CMP–Sialic Acid: Lactosylceramide–Sialyltransferase Activity in Cultured Hamster Cells." Biochim. Biophys. Acta., 804(4):442–449.
Carlson et al. (1973). J. Biol. Chem. 248(16) 5742–5750.
Cassels, Frederick J., et al. (1989). "Isolation of a Coaggregation–Inhibiting Cell Wall Polysaccharide from *Streptococcus sanguis* H1." Journal of Bacteriology, 171(7):4019–4025.
Ching, C.K., et al. (1990). "Purification and Characterization of a Peanut–Agglutination–Binding Pancreatic–Cancer–Related Serum Mucus Glycoprotein." Int. J. Cancer, 45:1022–1027.
Dabkowski et al. (1993). Transplant Proc., 25:2921.
David, et al. (1987), "Immobilized enzymes in preparative carbohydrate chemistry." Pure & Applied Chem. 59(11):1501–1508.
Deluca, et al. (1995). J. Am. Chem. Soc. 117:5869–5870.
Derwent Publications Ltd., London, GB; AN 90–135674 & JP–A–02 83 337 (Nichirei KK) Mar. 23, 1990. Abstract.
Eggens, Ivan et al. (1989). "Specific Interaction between Le$^x$ and Le$^x$ Determinants." J. Biol. Chem., 264 (16):9476–9484.
Finne, Jukka, et al. (1989). "Novel Polyfucosylated N–Linked Glycopeptides with Blood Group A,H,X and Y Determinants from Human Small Intestinal Epithelial Cells." J. Biol. Chem., 264(10):5720–5735.
Fukuda, Michiko N., et al. (1986). "Structure of a Novel Pialylated Fucosyl Lacto–N–nor–hexaosylceramide Isolated from Chronic Myelogenous Leukemia Cells." J. Biol. Chem., 261(5):2376–2383.
Fukushi, Yasuo, et al. (1984). "Novel Fucolipids Accumulating in Human Adenocarcinoma." J. Biol. Chem., 259(16):10511–10517.
Gamble, Jennifer R., et al. (1990). "Prevention of Activated Neutraphil Adhesion to Endothelium by Soluble Adhesion Protein GNP140." Science, 249:414–417.
Gillespie, et al. (1992). J. Biol. Chem., 267:21004.
Goelz, Susan E. (1990). "ELFT: A Gene That Directs the Expression of an ELAM–1 Ligand." Cell, 63:1349–1356.
Graber, Norma, et al. (1990). "T Cells Bind to Cytokine–Activated Endothelial Cells via a Novel, Inducible Sialoglycoprotein and Endothelial Leukocyte Adhesion Molecule–1." Journal of Immunology, 145:819–830.

(List continued on next page.)

*Primary Examiner*—Ponnathapu Achutamurthy
*Assistant Examiner*—Tekchand Saidha
*Attorney, Agent, or Firm*—Townsend and Townsend and Crew

[57] ABSTRACT

DNA sequences encoding GDP-fucose pyrophosphorylase (GTP+fucose-1-P→GDP-fucose+PP$_i$), are provided. The enzymes can be used in the synthesis of desired carbohydrate structures.

10 Claims, No Drawings

OTHER PUBLICATIONS

Gross, et al. (1987). Eur. J. Biochem., 168:595.

Hakomori, Sen–itiroh (1985). "Aberrant Glycosylation in Cancer Cell Membranes as Focused on Glycolipids: Overview and Perspectives." Cancer Research 45:2405–2414.

Hakomori, et al. (1984). J. Biol. Chem., 259(7):4672–4680.

Hansson, Gunnar, C., et al. (1983). "Mouse Monoclonal Antibodies against Human Cancer Cell Lines with Specificities for Blood Group and Related Anitgens." J. Biol. Chem., 258(7):4091–4097.

Hautanen, Aarno et al. (1989). "Effects of Modifications of the RGD Sequence and Its Context on Recognition by the Fibronectin Receptor." J. Biol. Chem., 264(3):1437–1442.

Higa, et al. (1985). J. Biol. Chem., 260(15):8838.

Holmes, Eric H., et al. (1985). "Enzymatic Basis for the Accumulation of Glycolipids with X and Dimeric X Determinants in Human Lung Cancer Cells (NCI–H69)." J. Biol. Chem., 260(12):7619–7627.

Ichikawa, et al. (1992). J. Am. Chem. Soc., 114:9283–9298.

Ichikawa et al. (1991). J. Am. Chem. Soc. 113(16):6300–6302.

Ichikawa, et al. (1991). J. A. Chem. Soc., 113:4698–4700.

Ito et al. (1993). Pure Appl. Chem., 65:753.

Johnson, Philip H., et al. (1985). "Sialyl compounds as acceptor substrates for the human r–3–and r–3/4–L–fucosyltransferases." Biochem. Soc. Trans., 13(6):1119–1120.

Kannagi, Reiji, et al. (1982). "Possible role of cermide in defining structure and function of membrane glycolipids." Proc. Natl. Acad. Sci USA, 79:3470–3474.

Koch, Alisa E., et al. (1991). "Immunolocalization of Endothelial and Leukocyte Adhesion Molecules in Human Rheumatoid and Osteoarthritic Synovial Tissues." Laboratory Investigation, 64(3):313–320.

Koshitomo, JP 62273919, Nov. 28, 1987. Chem. Abst. 109:66886.

Kurosawa, et al. (1994). Eur. J. Biochem., 219:375–381.

Lasky, Laurence A., et al. (1991). "The Lectin Cell Adhesion Molecules (LEC–CAMs): A New Family of Cell Adhesion Proteins Involve with Inflammation." Journal of Cell Biochemistry, 45(2):139–146.

Leeuwenberg, Jet F.M., et al. (1990). "IFN–: Regulates the Expression of the Adhesion Molecule Elam–1 and IL–6 Production by Human Endothelial Cells In Vitro." Journal of Immunology, 145:2110–2114.

Levery, Steven B., et al. (1988). "H–N.M.R. Analysis of Type–2 Chain Lacto–Gangliosides. Confirmation of Structure of a Novel Cancer–Associated Fucoganglioside." Carbohydrate Research, 178:121–144.

Livingston et al. (1993). J. Biol. Chem., 268:11504.

Lowe et al. Cell, Nov. 2, 1990, 63:475–484.

McIntire, Floyd C., et al. (1988). "A Polysaccharide from *Streptococcus sanguis* 34 inhibits Coaggregation of *S. sanguis* 34 with Actinomyces viscosus T14V." Journal of Bacteriology, 170(50): 2229–2235.

Nilsson, Kurt G.I. (1988). "Enzymatic synthesis of oligosaccharides." Trends in Biotechnology. 6:256–264.

Nunez, H.A. et al. (1976). "The Metal Ion Catalyzed Decomposition of Nucleoside Diphosphate Sugars." Biochemistry, 15(17):3843–3847.

Osborn, Laurelee, (1990). "Leukocyte Adhesion to Endothelium in Inflammation." Cell, 62:3–6.

Parmentier, Sophie, et al. (1991). "Inhibition of Platelet Functions by a Monclonal Antibody (LYP20) Directed Against a Granule Membrane Glycoprotein (GMP–140/PADGEM)." Blood, 77(8):1734–1739.

Phillips et al. Science, 250:1130 (1990); see, also, U.S.S.N. 08/063,181.

Picker, Louis J., et al. (1991). "The Neutrophil Selectin LECAM–1 Present Carbohydrate Ligands to the Vascular SElectins ELAM–1 and GMP–140." Cell 66:921–933.

Picker, Louis J., et al. (1991). "ELAM–1 is an adhesion molecule for skin–homing T cells." Nature, 349:796–799.

Polley et al. (1991). Proc. Natl. Acad. Sci., USA, 88:6224.

Preuss et al. (1993). J. Biol. Chem., 268:26273–78.

Rearick, et al. (1979). J. Biol. Chem., 254:4444.

Rosen, Steven D., et al. (1986). "Lymphocyte attachment to high endothelial venules during recirculation: A possible role for carbohydrates as recognition determinants." Molecular and Cellular Biochemistry, 72:153–164.

Sakurai, Yoichi (1989). "Production and clinical application of monoclonal anitbodies NCC–CO–450, –473 reactive with high–molecular–weight glycoprotein circulating in body fluid of gastroiintestinal cancer patents." (Abstract), Immunochemistry, 111:531; Chemical Abstracts, 111:151639b.

Shames, et al. (1991). Glycobiology, 1:187.

Shimizu, Yoji, et al. (1991). "Activation–independent binding of human memory T cells to adhesion molecule ELAM–1." Nature, 349:799–802.

Shitara, Kenya et al. (1991). "Application of Anti–Sialyl $Le^a$ Monoclonal antibody, KM231, for Immunotherapy of Cancer." Anticancer Research, 11:2003–2014.

Simon et al. (1988). J. Am. Chem. Soc., 110:7159.

Skinner, Michael P., et al. (1991). "GMP–140 Binding to Neutrophils Is Inhibited by Sulfated Glycans." J. Biol. Chem., 266(9):5371–5374.

Springer, Timothy A. (1990). "Adhesion receptors of the immune system." Nature, 346:425–434.

Tiemeyer, Michael, et al. (1991). "Carbohydrate ligands for endothelial–leukocyte adhesion molecule 111." Proc. Nat. Acad. Sci., 88:1138–1142.

Tyrrell, David, et al. (1991). "Structural requirements for the carbohydrate ligand of E–selectin." Proc. Nat. Acad. Sci.USA, 88:10372–10376.

Underhill, Charles, et al. (1978). "The Role of Hyaluronic Acid in Intercellular Adhesion of Cultured Mouse Cells." Experimental Cell Research, 117:155–164).

Van den Eijnden, et al. (1981). J. Biol. Chem., 256:3159.

Vann, et al. (1987). J. Biol. Chem., 262:17556.

Vijay, et al. (1975). J. Biol. Chem., 250(1):164.

Waltz, Gerd, et al. (1990). "Recognition by ELAM–1 of the Sialyl–$Le^x$ Determinant on Myeloid and Tumor Cells." Science, 250:1132–1135.

Weinstein, et al. (1982). J. Biol. Chem., 257:13845.

Wen et al. (1992). J. Biol. Chem., 267:21011.

Wong, Chi–Huey et al. (1992). "Regeneration of Sugar Nucelotide for Enzymatic Oligosaccharide Synthesis: Use of Gal–1–Phosphate Uridyltransferase in the Regeneration of UDP–Galactose, UDP–2–Deoxygalactose, and UDP–Galactosamine."J. Org. Chem., 57(16):4343–4344.

Yamamoto et al. (1990). Nature, 345:229–233.

Zapata, et al. (1990). J. Biol. Chem., 264(25):14769.

Zetter, Bruce R., (1990). "The Cellular Basis of Site–Specific Tumor Metastasis." The New England Journal of Medicine, 322(9):605–612.

Zhou, Qun, et al. (1991). "The Selectin GMP–140 Binds to Sialylated, Fucosylated Lactosaminolglycans on Both Myeloid and Nonmyeloid Cells." J. Cell Biol., 115(2):557–564.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2318 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 38..1822
      (D) OTHER INFORMATION: /product= "guanosine
         5-diphospho-beta-L-fucose (GDP-fucose)
         pyrophosphorylase (GDPFPP)"

(xi) SEQUENCE DESCRIPTION: SEQ ID NO:1:

```
GCGTGCTGTG CGGCGCGGTC TCAGGGAAGG TGGGGCT ATG GCA GCT GCT AGG GAC         55
                                        Met Ala Ala Ala Arg Asp
                                         1               5

CCT CCG GAA GTA TCG CTG CGA GAA GCC ACC CAG CGA AAA TTG CGG AGG          103
Pro Pro Glu Val Ser Leu Arg Glu Ala Thr Gln Arg Lys Leu Arg Arg
            10                  15                  20

TTT TCC GAG CTA AGA GGC AAA CTT GTA GCA CGT GGA GAA TTC TGG GAC          151
Phe Ser Glu Leu Arg Gly Lys Leu Val Ala Arg Gly Glu Phe Trp Asp
        25                  30                  35

ATA GTT GCA ATA ACA GCG GCT GAT GAA AAA CAG GAA CTT GCT TAC AAC          199
Ile Val Ala Ile Thr Ala Ala Asp Glu Lys Gln Glu Leu Ala Tyr Asn
    40                  45                  50

CAA CAG CTG TCA GAA AAG CTG AAA AGA AAG GAG TTA CCC CTT GGA GTT          247
Gln Gln Leu Ser Glu Lys Leu Lys Arg Lys Glu Leu Pro Leu Gly Val
55                  60                  65                  70

CAA TAT CAC GTT TTT GTG GAT CCT GCT GGA GCC AAA ATT GGA AAT GGA          295
Gln Tyr His Val Phe Val Asp Pro Ala Gly Ala Lys Ile Gly Asn Gly
                75                  80                  85

GGA TCA ACA CTT TGT GCC CTT CAA TGT TTG GAA AAG CTA TAT GGA GAT          343
Gly Ser Thr Leu Cys Ala Leu Gln Cys Leu Glu Lys Leu Tyr Gly Asp
            90                  95                 100

AAA TGG AAT TCT TTT ACC ATC TTA TTA ATT CAC TCT GGT GGC TAC AGT          391
Lys Trp Asn Ser Phe Thr Ile Leu Leu Ile His Ser Gly Gly Tyr Ser
       105                 110                 115

CAA CGA CTT CCA AAT GCA AGT GCT CTG GGA AAA ATT TTC ACT GCT TTA          439
Gln Arg Leu Pro Asn Ala Ser Ala Leu Gly Lys Ile Phe Thr Ala Leu
   120                 125                 130

CCT CTT GGT AAC CCC ATT TAT CAG ATG CTA GAA TTA AAG CTA GCC ATG          487
Pro Leu Gly Asn Pro Ile Tyr Gln Met Leu Glu Leu Lys Leu Ala Met
```

```
            135                 140                 145                 150
TAC ATT GAT TTC CCC TTA AAT ATG AAT CCT GGA ATT CTG GTT ACC TGT                535
Tyr Ile Asp Phe Pro Leu Asn Met Asn Pro Gly Ile Leu Val Thr Cys
            155                 160                 165

GCA GAT GAT ATT GAA CTT TAT AGT ATT GGA GAA TTT GAG TTT ATT AGG                583
Ala Asp Asp Ile Glu Leu Tyr Ser Ile Gly Glu Phe Glu Phe Ile Arg
            170                 175                 180

TTT GAC AAA CCT GGC TTT ACT GCT TTA GCT CAT CCT TCT AGT TTG ACG                631
Phe Asp Lys Pro Gly Phe Thr Ala Leu Ala His Pro Ser Ser Leu Thr
            185                 190                 195

ATA GGT ACC ACA CAT GGA GTA TTT GTC TTA GAT CCT TTT GAT GAT TTA                679
Ile Gly Thr Thr His Gly Val Phe Val Leu Asp Pro Phe Asp Asp Leu
            200                 205                 210

AAA CAT AGA GAC CTT GAA TAC AGG TCT TGC CAT CGT TTC CTT CAT AAG                727
Lys His Arg Asp Leu Glu Tyr Arg Ser Cys His Arg Phe Leu His Lys
215                 220                 225                 230

CCC AGC ATA GAA AAG ATG TAT CAG TTT AAT GCT GTG TGT AGA CCT GGA                775
Pro Ser Ile Glu Lys Met Tyr Gln Phe Asn Ala Val Cys Arg Pro Gly
            235                 240                 245

AAT TTT TGT CAA CAG GAC TTT GCT GGG GGT GAC ATT GCC GAT CTT AAA                823
Asn Phe Cys Gln Gln Asp Phe Ala Gly Gly Asp Ile Ala Asp Leu Lys
            250                 255                 260

TTA GAC TCT GAC TAT GTC TAC ACA GAT AGC CTA TTT TAT ATG GAT CAT                871
Leu Asp Ser Asp Tyr Val Tyr Thr Asp Ser Leu Phe Tyr Met Asp His
            265                 270                 275

AAA TCA GCA AAA ATG TTA CTT GCT TTT TAT GAA AAA ATA GGC ACA CTG                919
Lys Ser Ala Lys Met Leu Leu Ala Phe Tyr Glu Lys Ile Gly Thr Leu
280                 285                 290

AGC TGT GAA ATA GAT GCC TAT GGT GAC TTT CTG CAG GCT TTG GGA CCT                967
Ser Cys Glu Ile Asp Ala Tyr Gly Asp Phe Leu Gln Ala Leu Gly Pro
295                 300                 305                 310

GGA GCA ACT GTG GAG TAC ACC AGA AAC ACA TCA CAT GTC ATT AAA GAA               1015
Gly Ala Thr Val Glu Tyr Thr Arg Asn Thr Ser His Val Ile Lys Glu
            315                 320                 325

GAG TCA GAG TTG GTA GAA ATG AGG CAG AGA ATA TTT CAT CTT CTT AAA               1063
Glu Ser Glu Leu Val Glu Met Arg Gln Arg Ile Phe His Leu Leu Lys
            330                 335                 340

GGA ACA TCA CTA AAT GTT GTT GTT CTT AAT AAC TCC AAA TTT TAT CAC               1111
Gly Thr Ser Leu Asn Val Val Val Leu Asn Asn Ser Lys Phe Tyr His
            345                 350                 355

ATT GGA ACA ACC GAA GAA TAT TTG TTT TAC TTT ACC TCA GAT AAC AGT               1159
Ile Gly Thr Thr Glu Glu Tyr Leu Phe Tyr Phe Thr Ser Asp Asn Ser
            360                 365                 370

TTA AAG TCA GAG CTC GGC TTA CAG TCC ATA ACT TTT AGT ATC TTT CCA               1207
Leu Lys Ser Glu Leu Gly Leu Gln Ser Ile Thr Phe Ser Ile Phe Pro
375                 380                 385                 390

GAT ATA CCA GAA TGC TCT GGC AAA ACA TCC TGT ATC ATT CAA AGC ATA               1255
Asp Ile Pro Glu Cys Ser Gly Lys Thr Ser Cys Ile Ile Gln Ser Ile
            395                 400                 405

CTG GAT TCA AGA TGT TCT GTG GCA CCT GGC TCA GTT GTG GAG TAT TCC               1303
Leu Asp Ser Arg Cys Ser Val Ala Pro Gly Ser Val Val Glu Tyr Ser
            410                 415                 420

AGA TTG GGG CCT GAT GTT TCA GTT GGG GAA AAC TGC ATT ATT AGT GGT               1351
Arg Leu Gly Pro Asp Val Ser Val Gly Glu Asn Cys Ile Ile Ser Gly
            425                 430                 435

TCT TAC ATC CTA ACA AAA GCT GCC CTC CCC GCA CAT TCT TTT GTA TGT               1399
Ser Tyr Ile Leu Thr Lys Ala Ala Leu Pro Ala His Ser Phe Val Cys
            440                 445                 450

TCC TTA AGC TTA AAG ATG AAT AGA TGC TTA AAG TAT GCA ACT ATG GCA               1447
```

```
Ser Leu Ser Leu Lys Met Asn Arg Cys Leu Lys Tyr Ala Thr Met Ala
455                 460                 465                 470

TTT GGA GTG CAA GAC AAC TTG AAA AAG AGT GTG AAA ACA TTG TCA GAT     1495
Phe Gly Val Gln Asp Asn Leu Lys Lys Ser Val Lys Thr Leu Ser Asp
                475                 480                 485

ATA AAG TTA CTT CAA TTC TTT GGA GTC TGT TTC CTG TCA TGC TTA GAT     1543
Ile Lys Leu Leu Gln Phe Phe Gly Val Cys Phe Leu Ser Cys Leu Asp
                490                 495                 500

GTT TGG AAT CTT AAA GTT ACA GAG GAA CTG TTC TCT GGT AAC AAG ACA     1591
Val Trp Asn Leu Lys Val Thr Glu Glu Leu Phe Ser Gly Asn Lys Thr
                505                 510                 515

TGT CTG AGT TTG TGG ACT GCA CGC ATT TTC CCA GTT TGT TCT TCT TTG     1639
Cys Leu Ser Leu Trp Thr Ala Arg Ile Phe Pro Val Cys Ser Ser Leu
520                 525                 530

AGT GAC TCA GTT ATA ACA TCC CTA AAG ATG TTA AAT GCT GTT AAG AAC     1687
Ser Asp Ser Val Ile Thr Ser Leu Lys Met Leu Asn Ala Val Lys Asn
535                 540                 545                 550

AAG TCA GCA TTC AGC CTG AAT AGC TAT AAG TTG CTG TCC ATT GAA GAA     1735
Lys Ser Ala Phe Ser Leu Asn Ser Tyr Lys Leu Leu Ser Ile Glu Glu
                555                 560                 565

ATG CTT ATC TAC AAA GAT GTA GAA GAT ATG ATA ACT TAC AGG GAA CAA     1783
Met Leu Ile Tyr Lys Asp Val Glu Asp Met Ile Thr Tyr Arg Glu Gln
                570                 575                 580

ATT TTT CTA GAA ATC AGT TTA AAA AGC AGT TTG ATG TAGAGATATT          1829
Ile Phe Leu Glu Ile Ser Leu Lys Ser Ser Leu Met
                585                 590

TTAAATATTG TACACTTTGC CTTTTTGAGT AACATTCCAG AGATAGGTAT TTTTGGTAGG   1889

CTGTTTCACT GAACTCAGTT AATGAAAACT GTATTAACAT AATTGTTGTA GCATAATATT   1949

AATAGTGCAA AAGTACATAT AAGTCATTTT GATGAAAAAT ATTCCAAGAC TAAGTTGAGA   2009

AAAGAGATAC TATTTTGGAT GTGTATCAGT ATTTTTGTTT TAATAATGA TTGATTTGTG    2069

GAGCATTGTT TTTTCACATA ATTAGTTTTA AAGGTAATTT TCTAAGCATA CCTTTGGAAT   2129

TTTTCCATCT TTTTTGAGGC TTTTGGTCCA GTGAAGTTCT AAGTATTCAC TGGCACTTCT   2189

CTCCTCAACT GTAATTCTAT TTTTAATAAT AAAAATGGCA TACTGTAGGG TCTTCAGAGT   2249

AGTGTAGGAA TACTGTAGAA ATACTTTTTC AGAAACGAAT CCATAGCTGA CAAATTCACT   2309

CAGTGCCCA                                                           2318

(2) INFORMATION FOR SEQ ID NO:2:

(i) SEQUENCE CHARACTERISTICS:
        (A) LENGTH: 594 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ala Ala Arg Asp Pro Pro Glu Val Ser Leu Arg Glu Ala Thr
1               5                   10                  15

Gln Arg Lys Leu Arg Arg Phe Ser Glu Leu Arg Gly Lys Leu Val Ala
                20                  25                  30

Arg Gly Glu Phe Trp Asp Ile Val Ala Ile Thr Ala Ala Asp Glu Lys
            35                  40                  45

Gln Glu Leu Ala Tyr Asn Gln Gln Leu Ser Glu Lys Leu Lys Arg Lys
        50                  55                  60

Glu Leu Pro Leu Gly Val Gln Tyr His Val Phe Val Asp Pro Ala Gly
65                  70                  75                  80
```

-continued

```
Ala Lys Ile Gly Asn Gly Gly Ser Thr Leu Cys Ala Leu Gln Cys Leu
                 85                  90                  95

Glu Lys Leu Tyr Gly Asp Lys Trp Asn Ser Phe Thr Ile Leu Leu Ile
            100                 105                 110

His Ser Gly Gly Tyr Ser Gln Arg Leu Pro Asn Ala Ser Ala Leu Gly
            115                 120                 125

Lys Ile Phe Thr Ala Leu Pro Leu Gly Asn Pro Ile Tyr Gln Met Leu
            130                 135                 140

Glu Leu Lys Leu Ala Met Tyr Ile Asp Phe Pro Leu Asn Met Asn Pro
145                 150                 155                 160

Gly Ile Leu Val Thr Cys Ala Asp Asp Ile Glu Leu Tyr Ser Ile Gly
                165                 170                 175

Glu Phe Glu Phe Ile Arg Phe Asp Lys Pro Gly Phe Thr Ala Leu Ala
            180                 185                 190

His Pro Ser Ser Leu Thr Ile Gly Thr Thr His Gly Val Phe Val Leu
            195                 200                 205

Asp Pro Phe Asp Asp Leu Lys His Arg Asp Leu Glu Tyr Arg Ser Cys
            210                 215                 220

His Arg Phe Leu His Lys Pro Ser Ile Glu Lys Met Tyr Gln Phe Asn
225                 230                 235                 240

Ala Val Cys Arg Pro Gly Asn Phe Cys Gln Gln Asp Phe Ala Gly Gly
                245                 250                 255

Asp Ile Ala Asp Leu Lys Leu Asp Ser Asp Tyr Val Tyr Thr Asp Ser
            260                 265                 270

Leu Phe Tyr Met Asp His Lys Ser Ala Lys Met Leu Leu Ala Phe Tyr
            275                 280                 285

Glu Lys Ile Gly Thr Leu Ser Cys Glu Ile Asp Ala Tyr Gly Asp Phe
290                 295                 300

Leu Gln Ala Leu Gly Pro Gly Ala Thr Val Glu Tyr Thr Arg Asn Thr
305                 310                 315                 320

Ser His Val Ile Lys Glu Glu Ser Glu Leu Val Glu Met Arg Gln Arg
                325                 330                 335

Ile Phe His Leu Leu Lys Gly Thr Ser Leu Asn Val Val Val Leu Asn
            340                 345                 350

Asn Ser Lys Phe Tyr His Ile Gly Thr Thr Glu Glu Tyr Leu Phe Tyr
            355                 360                 365

Phe Thr Ser Asp Asn Ser Leu Lys Ser Glu Leu Gly Leu Gln Ser Ile
            370                 375                 380

Thr Phe Ser Ile Phe Pro Asp Ile Pro Glu Cys Ser Gly Lys Thr Ser
385                 390                 395                 400

Cys Ile Ile Gln Ser Ile Leu Asp Ser Arg Cys Ser Val Ala Pro Gly
                405                 410                 415

Ser Val Val Glu Tyr Ser Arg Leu Gly Pro Asp Val Ser Val Gly Glu
            420                 425                 430

Asn Cys Ile Ile Ser Gly Ser Tyr Ile Leu Thr Lys Ala Ala Leu Pro
            435                 440                 445

Ala His Ser Phe Val Cys Ser Leu Ser Leu Lys Met Asn Arg Cys Leu
450                 455                 460

Lys Tyr Ala Thr Met Ala Phe Gly Val Gln Asp Asn Leu Lys Lys Ser
465                 470                 475                 480

Val Lys Thr Leu Ser Asp Ile Lys Leu Leu Gln Phe Phe Gly Val Cys
                485                 490                 495
```

```
Phe Leu Ser Cys Leu Asp Val Trp Asn Leu Lys Val Thr Glu Glu Leu
            500                 505                 510

Phe Ser Gly Asn Lys Thr Cys Leu Ser Leu Trp Thr Ala Arg Ile Phe
            515                 520                 525

Pro Val Cys Ser Ser Leu Ser Asp Ser Val Ile Thr Ser Leu Lys Met
530                     535                 540

Leu Asn Ala Val Lys Asn Lys Ser Ala Phe Ser Leu Asn Ser Tyr Lys
545                 550                 555                 560

Leu Leu Ser Ile Glu Glu Met Leu Ile Tyr Lys Asp Val Glu Asp Met
                565                 570                 575

Ile Thr Tyr Arg Glu Gln Ile Phe Leu Glu Ile Ser Leu Lys Ser Ser
                580                 585                 590

Leu Met (2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Thr Glu Glu Leu Phe Ser Gly Asn Lys Thr Cys Leu Ser Leu Trp Thr
1               5                   10                  15

Ala Arg Ile Phe
            20

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TCAGATATCG GGGCTATGGC AGCTGCTAG                                   29

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ATAGATATCT CTGGAATGTT ACTCAAAAAG GCAA                             34
```

NUCLEIC ACIDS ENCODING GDP-FUCOSE PYROPHOSPHORYLASE

CROSS-REFERENCE TO RELATED APPLICATIONS

This application claims priority from U.S. provisional application Ser. No. 60/015,241, filed Apr. 10, 1996, incorporated by reference. In addition, this application is related to copending application Ser. No. 08/628,543 for "Improved Enzymatic Synthesis of Oligosaccharides" and Ser. No. 08/628,545 for "Improved Enzymatic Synthesis of Glycosidic Linkages", both filed on Apr. 10, 1996, which are incorporated by reference.

FIELD OF THE INVENTION

The present invention relates to isolated GDP-fucose pyrophosphorylase enzymes and nucleic acids encoding them. The enzymes are particularly useful in the synthesis of oligosaccharides.

BACKGROUND OF THE INVENTION

Increased understanding of the role of carbohydrates as recognition elements on the surface of cells has led to increased interest in the production of carbohydrate molecules of defined structure. For instance, compounds comprising the sialyl Lewis ligands, sialyl Lewis$^x$ and sialyl Lewis$^a$ are present in leukocyte and non-leukocyte cell lines that bind to receptors such as the ELAM-1 and GMP 140 receptors. Polley et al., *Proc. Natl. Acad. Sci., USA*, 88:6224 (1991) and Phillips et al., *Science*, 250:1130 (1990), see, also, U.S. Ser. No. 08/063,181.

Because of interest in making desired carbohydrate structures, glycosyltransferases and their role in enzyme-catalyzed synthesis of carbohydrates are presently being extensively studied. These enzymes exhibit high specificity and are useful in forming carbohydrate structures of defined sequence. Consequently, glycosyltransferases are increasingly employed as enzymatic catalysts in the synthesis of a number of carbohydrates used for therapeutic and other purposes (Ito et al., *Pure Appl. Chem.*, 65:753 (1993); U.S. Pat. Nos. 5,352,670, and 5,374,541).

Synthesis of desired carbohydrate compounds has been achieved on preparative scales using enzymatic cycles using glycosyltransferases such as β1,4 galactosyltransferase and α2,3 sialyltransferase (See, e.g., U.S. Pat. No. 5,374,541; WO 9425615; and Ichikawa, et al., *J. Am. Chem. Soc.*, 114:9283–9298 (1992)).

Although fucosyltransferases have been cloned and expressed, enzymes for the production of guanosine 5-diphospho-β L-fucose (GDP-fucose), the donor substrate for the fucosyltransferases are not readily available. Use of fucosyltransferase cycles would be greatly facilitated if GDP-fucose can be readily regenerated enzymatically. The present invention fulfills these and other needs.

SUMMARY OF THE INVENTION

The present invention provides compositions comprising isolated GDP-fucose pyrophosphorylase (GDPFPP) enzymes as well as nucleic acids that encode them.

The proteins of the invention can be derived from a variety of sources and specifically bind to antibodies generated against a protein having a sequence as shown in SEQ ID NO:2. A particular example of the proteins of the invention is provided: a protein that has GDP-fucose pyrophosphorylase activity as defined herein, a molecular weight of approximately 66 kD, and a sequence as shown in SEQ. ID. No. 2.

The nucleic acids of the invention can be derived from a variety of sources and typically hybridize under stringent conditions to a nucleic acid with a sequence as shown in SEQ ID NO: 1. The nucleic acids may be incorporated into appropriate recombinant DNA construct comprising a promoter operably linked to the nucleic acid. The promoter can be selected to direct expression of in any desired cell, e.g., mammalian cells, insect cells, fungal cells, and the like.

The invention further comprises compositions and kits that contain (alone, or in combination): oligonucleotides that specifically hybridize to SEQ ID NO:1 under stringent conditions, antibodies or antisera that specifically bind to SEQ ID NO:2, and a protein that specifically cross-reacts with SEQ ID NO:2 and has GDPFPP activity.

Definitions

As used herein, "GDP-fucose pyrophosphorylase" is an isolated polypeptide or protein preparation capable of catalyzing the following reaction: GTP+fucose I-P→GDP-fucose+$PP_i$. The term further refers to, and explicitly encompasses, proteins that specifically cross-react with specific antisera to SEQ ID NO:2.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company. In addition, individual substitutions, deletions or additions which alter, add or delete a single amino acid or a small percentage of amino acids in an encoded sequence are also "conservatively modified variations".

The term "isolated" is meant to refer to material which is substantially or essentially free from components which normally accompany the enzyme as found in its native state. Thus, the enzymes of the invention do not include materials normally associated with their in situ environment. Typically, isolated proteins of the invention are at least about 80% pure, usually at least about 90%, and preferably at least about 95% as measured by band intensity on a silver stained gel. The polypeptides may be purified from transgenic cells or cells which they are naturally expressed.

An example of the GDP-fucose pyrophosphorylase enzymes of the invention is a protein that has a molecular weight of about 66 kD and GDPFPP activity. GDPFPP enzymatic activity can be assayed in a number of ways. Three preferred assays are presented in detail below. An isolated, purified GDPFPP of the invention will generally catalyze the production of GDP-fucose from GTP and fucose 1-phosphate under conditions described in assay #2.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The term "substantial identity" means that a polypeptide comprises a sequence that has at least 80% sequence identity, preferably 90%, more preferably 95% or more, compared to a reference sequence over a comparison window of about 20 residues to about 600 residues—typically about 50 to about 500 residues usually about 250 to 300 residues. The values of percent identity are determined using the programs above.

Another indication that polypeptide sequences are substantially identical is if one protein is immunologically reactive with antibodies raised against the other protein. Thus, the GDPFPP enzymes of the invention include polypeptides immunologically reactive with antibodies raised against a protein having a sequence as shown in SEQ. ID. No. 2. The phrase "specifically binds to an antibody" or "specifically immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) ANTIBODIES, A LABORATORY MANUAL, Cold Spring Harbor Publications, New York, for a description of immunoassay formats and conditions that can be used to determine specific immunoreactivity.

Another indication that nucleotide sequences are substantially identical is if two molecules hybridize to each other under stringent conditions. Stringent conditions are sequence-dependent and will be different in different circumstances. Generally, stringent conditions are selected to be about 5° to about 20° C., usually about 10° C. to about 15° C., lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For instance in a standard Southern hybridization procedure, stringent conditions will include an initial wash in 6× SSC at 42° C. followed by one or more additional washes in 0.2×SSC at a temperature of at least about 55° C., typically about 60° C. and often about 65° C.

Nucleotide sequences are also substantially identical for purposes of this application when the polypeptides which they encode are substantially identical. Thus, where one nucleic acid sequence encodes essentially the same polypeptide as a second nucleic acid sequence, the two nucleic acid sequences are substantially identical, even if they would not hybridize under stringent conditions due to silent substitutions permitted by the genetic code (see, Darnell et al. (1990) *Molecular Cell Biology*, Second Edition *Scientific American Books* W. H. Freeman and Company New York for an explanation of codon degeneracy and the genetic code).

Protein purity or homogeneity may be indicated by a number of means well known in the art, such as polyacrylamide gel electrophoresis of a protein sample, followed by visualization upon staining. For certain purposes high resolution will be needed and HPLC or a similar means for purification utilized.

The term "residue" refers to an amino acid (D or L) or amino acid mimetic incorporated in a oligopeptide by an amide bond or amide bond mimetic. An amide bond mimetic of the invention includes peptide backbone modifications well known to those skilled in the art.

DETAILED DESCRIPTION OF THE INVENTION

The present invention provides isolated GDP-fucose pyrophosphorylase (GDPFPP) and nucleic acids encoding the enzyme. The nucleic acids are used to recombinantly express the enzyme, which can be used in a variety of applications. A particularly useful application is for regeneration of GDP-fucose in fucosyltransferase cycles in the synthesis of carbohydrates.

Little is known about the enzymes involved in the metabolism of GDP-fucose. In most organisms, GDP-fucose is formed from GDP-mannose by the sequential action of three distinct enzymatic activities: GDP-D-mannose 4,6-dehydratase, and a single protein that accomplishes epimerization and reduction, GDP-4-keto-6-deoxy-D-mannose-3,5-epimerase-4-reductase (Ginsburg, et al., *J. Biol. Chem.*, 236, 2389–2393 (1961) and Chang, et al., *J. Biol. Chem.*, 263, 1693–1697 (1988)). A minor or "scavenge" pathway also exists, in which free fucose is phosphorylated by fucokinase to form fucose 1-phosphate, which, along with guanosine 5'-triphosphate (GTP), is used by GDP-fucose pyrophosphorylase to form GDP-fucose (Ginsburg, et al., *J. Biol. Chem.*, 236, 2389–2393 (1961) and Reitman, *J. Biol. Chem.*, 255, 9900–9906 (1980)).

The enzymes of the invention are particularly useful in methods for the formation of a glycosidic linkage which takes place in a reaction medium comprising at least one glycosyl transferase (e.g., fucosyltransferase), a donor substrate (e.g., GDP-fucose) which is usually formed during the reaction by the action of the GDPFPP, an acceptor sugar and a divalent metal cation. The methods rely on the use of a glycosyl transferase to catalyze the addition of a saccharide to a substrate saccharide. The addition takes place at the non-reducing end of an oligosaccharide or carbohydrate moiety on a biomolecule. Biomolecules as defined here include but are not limited to biologically significant molecules such as proteins (e.g., glycoproteins), and lipids (e.g., glycolipids, phospholipids, sphingolipids and gangliosides). In these methods, the divalent metal ion concentration is typically supplemented during the formation of the glycosidic linkage to replenish the concentration of the metal cation in the reaction medium between about 2 mM and about 75 mM.

The following abbreviations are used herein:

Ara=arabinosyl;

Fru=fructosyl;
Fuc=fucosyl;
Gal=galactosyl;
GalNAc=N-acetylgalacto;
Glc=glucosyl;
GlcNAc=N-acetylgluco;
Man=mannosyl; and
NeuAc=sialyl (N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose.

A. General Methods

Much of the nomenclature and general laboratory procedures required in this application can be found in Sambrook, et al., *MOLECULAR CLONING A LABORATORY MANUAL* (2nd Ed.), Vol. 1–3, Cold Spring Harbor Laboratory, Cold Spring Harbor, N.Y., 1989. The manual is hereinafter referred to as "Sambrook, et al."

The practice of this invention involves the construction of recombinant nucleic acids and the expression of genes in transfected cells. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, GUIDE TO MOLECULAR CLONING TECHNIQUES, *Methods in Enzymology* volume 152 Academic Press, Inc., San Diego, Calif. (Berger); and CURRENT PROTOCOLS IN MOLECULAR BIOLOGY, F. M. Ausubel et al., eds., Current Protocols, a joint venture between Greene Publishing Associates, Inc. and John Wiley & Sons, Inc., (1994 Supplement) (Ausubel).

Examples of techniques sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al., (1987) U.S. Pat. No. 4,683,202; PCR PROTOCOLS A GUIDE TO METHODS AND APPLICATIONS (Innis et al. eds) Academic Press Inc. San Diego, Calif. (1990) (Innis); Arnheim & Levinson (Oct. 1, 1990) C&EN 36–47; *The Journal of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; and Barringer et al. (1990) *Gene* 89, 117. Improved methods of cloning in vitro amplified nucleic acids are described in Wallace et al., U.S. Pat. No. 5,426,039.

The culture of cells used in the present invention, including cell lines and cultured cells from tissue or blood samples is well known in the art. Freshney (*Culture of Animal Cells, a Manual of Basic Technique*, third edition Wiley-Liss, New York (1994)) and the references cited therein provides a general guide to the culture of cells.

B. Methods for Isolating DNA Encoding GDPFPP

The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

Techniques for manipulation of nucleic acids encoding the enzymes of the invention, such as subcloning nucleic acid sequences encoding polypeptides into expression vectors, labelling probes, DNA hybridization, and the like are described generally in Sambrook et al.

Recombinant DNA techniques can be used to produce GDPFPP. In general, the DNA encoding the enzymes are first cloned or isolated in a form suitable for ligation into an expression vector. After ligation, the vectors containing the DNA fragments or inserts are introduced into a suitable host cell for expression of the recombinant enzymes. The enzymes are then isolated from the host cells.

There are various methods of isolating the DNA sequences encoding GDPFPP. Typically, the DNA is isolated from a genomic or cDNA library using labelled oligonucleotide probes specific for sequences in the DNA. The DNA libraries can be prepared from any organism or cell type that produces the enzymes. For instance, both prokaryotic and eukaryotic organisms can be used. Typically the nucleic acids are prepared from mammalian cells or tissue. The particular species from which the nucleic acids are isolated is not critical so long as enzymes of sufficient activity are encoded. Suitable sources include human, rat, mouse, rabbit, pig, and other mammals. Other organisms that can be used include *Caenorhabditis elegans*, the slime mold *Dictyostelium discoideum*, plants such as *Zea mays, Arabidopsis thaliana, Vigna radiata* (mung bean), algae such as *Fucus gardnieri*, bacteria such as but not limited to: *Mycobaterium gardnieri, Mycobacterium szulgai, Mycobacterium avium*, and *Mycobacterium tuberculosis, Neisseria gonorrhoeae, Neisseria Meningitidis*, and *Nesseria lactamica, Helicobacter pylori, Streptococcus pyogenes*, the fungi: *Candida albicans, Schizosaccaromyces pombe, Aspergillus niger, Aspergillus nidulans*, the fruit fly *Drosophila melanogaster*, amphibians such as *Xenopus laevis*, etc. The sequence of the probes used to isolate the nucleic acids is based on the nucleic acid sequences disclosed here. If cDNA libraries are used, mRNA from kidney or thyroid tissue is typically used to prepare the cDNA (However, GDPFPP mRNA is ubiquitously expressed in all tissues assayed by Northern blot using a human cDNA probe, and any tissue that express the mRNA may be used).

The polymerase chain reaction can also be used to prepare the DNA. Polymerase chain reaction technology (PCR) is used to amplify GDPFPP nucleic acid sequences directly from mRNA, from cDNA, and from genomic libraries or cDNA libraries.

Appropriate primers and probes for amplifying the GDPFPP DNA's are generated from analysis of the DNA sequences. In brief, oligonucleotide primers that are complementary to the DNA sequences located on both sides of the region to be amplified are synthesized. The polymerase chain reaction is then carried out using the two primers. See PCR PROTOCOLS: A GUIDE TO METHODS AND APPLICATIONS. (Innis, M, Gelfand, D., Sninsky, J. and White, T., eds.), Academic Press, San Diego (1990). Primers can be selected to amplify the entire gene or to amplify smaller segments, as desired. Preferred probes for this purpose are 5'-TCA-GAT-ATC-GGG-GCT-ATG-GCA-GCT-GCT-AG-3' and 5'-ATA-GAT-ATC-TCT-GGA-ATG-TTA-CTC-AAA-AAG-GCA-A-3', respectively.

Oligonucleotides for use as probes and primers are chemically synthesized according to the solid phase phosphoramidite triester method first described by Beaucage, S. L. and Caruthers, M. H., (1981) *Tetrahedron Letts.*, 22(20) :1859–1862 using an automated synthesizer, as described in Needham-VanDevanter, D. R., et al. 1984, *Nucleic Acids Res.*, 12:6159–6168. Purification of oligonucleotides is by either native acrylamide gel electrophoresis or by anion-exchange HPLC as described in Pearson, J. D. and Regnier, F. E. (1983), *J. Chrom.*, 255:137–149.

The sequence of the synthetic oligonucleotides can be verified using the chemical degradation method of Maxam, A. M. and Gilbert, 1980, in W., Grossman, L. and Moldave, D., eds. Academic Press, New York, Methods in Enzymology, 65:499–560.

Other methods known to those of skill in the art may also be used to isolate DNA encoding all or part of the GDPFPP enzyme. See Sambrook, et al.

C. Expression of GDPFPP

Once desired DNAs are isolated and cloned, one may express the desired polypeptides in a recombinantly engineered cell such as bacteria, fungus (including yeast), insect (especially employing baculoviral vectors), and mammalian cells. It is expected that those of skill in the art are knowledgeable in the numerous expression systems available for expression of the DNA encoding the enzymes. No attempt to describe in detail the various methods known for the expression of proteins in prokaryotes or eukaryotes will be made.

In brief summary, the expression of natural or synthetic nucleic acids encoding GDPFPP will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the enzymes. To obtain high level expression of a cloned gene, it is desirable to construct expression plasmids which contain, at the minimum, a strong promoter to direct transcription, a ribosome binding site for translational initiation, and a transcription/translation terminator.

1. Expression in Prokaryotes

Examples of regulatory regions suitable for this purpose in *E. coli* are the promoter and operator region of the *E. coli* tryptophan biosynthetic pathway as described by Yanofsky, C., 1984, *J. Bacteriol.*, 158:1018–1024 and the leftward promoter of phage lambda ($P_L$) as described by Herskowitz, I. and Hagen, D., 1980, *Ann. Rev. Genet.*, 14:399–445. The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA.

Expression systems for expressing the enzymes are available using *E. coli*, *Bacillus* sp. (Palva, I. et al., 1983, *Gene* 22:229–235; Mosbach, K. et al., *Nature* 302:543–545 and *Salmonella*. *E. coli* systems are preferred.

The polypeptides produced by prokaryote cells may not necessarily fold properly. During purification from *E. coli*, the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration. U.S. Pat. No. 4,511,503.

Detection of the expressed enzyme is achieved by methods known in the art as radioimmunoassays, Western blotting techniques, immunoprecipitation, or activity assays. Purification from *E. coli* can be achieved following procedures described in U.S. Pat. No. 4,511,503.

2. Expression in Eukaryotes

A variety of eukaryotic expression systems such fungal cells (particularly yeast), insect cell lines and mammalian cells, are known to those of skill in the art. As explained briefly below, the enzymes may also be expressed in these eukaryotic systems.

a. Expression in Fungal Cells, Including Yeast

In addition to use in recombinant expression systems, the isolated GDPFPP DNA sequences can also be expressed in fungal cells.

Techniques for transforming fungi are well known in the literature, and have been described, for instance, by Beggs, Hinnen et al. (*Proc. Natl. Acad. Sci. USA* 75: 1929–1933 (1978)), Yelton et al. (*Proc. Natl. Acad. Sci. USA* 81: 1740–1747 (1984)), and Russell (*Nature* 301: 167–169 (1983)). Typically, filamentous fungi, for example, strains of the fungi Aspergillus (McKnight et al., U.S. Pat. No. 4,935,349) are used. Examples of useful promoters include those derived from *Aspergillus nidulans* glycolytic genes, such as the ADH3 promoter (McKnight et al., *EMBO J.* 4: 2093–2099 (1985)) and the tpiA promoter. An example of a suitable terminator is the ADH3 terminator (McKnight et al.). The expression units utilizing such components are cloned into vectors that are capable of insertion into the chromosomal DNA of Aspergillus.

Synthesis of heterologous proteins in yeast is well known and described in the literature. *Methods in Yeast Genetics*, Sherman, F., et al., Cold Spring Harbor Laboratory, (1982) is a well recognized work describing the various methods available to produce the enzymes in yeast.

Examples of promoters for use in yeast include GAL1,10 (Johnson, M., and Davies, R. W., 1984, *Mol. and Cell. Biol.*, 4:1440–1448) ADH2 (Russell, D., et al. 1983, *J. Biol. Chem.*, 258:2674–2682), PH05 (EMBO J. 6:675–680, 1982), and MFα1 (Herskowitz, I. and Oshima, Y., 1982, in THE MOLECULAR BIOLOGY OF THE YEAST SACCHAROMYCES, (eds. Strathern, J. N. Jones, E. W., and Broach, J. R., Cold Spring Harbor Lab., Cold Spring Harbor, N.Y., pp. 181–209. A multicopy plasmid with a selective marker such as Leu-2, URA-3, Trp-1, and His-3 is also desirable.

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., 1979, *Gene*, 8:17–24; Broach, et al., 1979, *Gene*, 8:121–133).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978, *Nature* (London), 275:104–109; and Hinnen, A., et al., 1978, *Proc. Natl. Acad. Sci. USA*, 75:1929–1933. The second procedure does not involve removal of the cell wall. Instead the cells are treated with lithium chloride or acetate and PEG and put on selective plates (Ito, H., et al., 1983, *J. Bact.*, 153:163–168).

The enzymes can be isolated from yeast by lysing the cells and applying standard protein isolation techniques to the lysates. The monitoring of the purification process can be accomplished by using Western blot techniques or radioimmunoassays of other standard immunoassay techniques.

b. Expression in Mammalian and Insect Cell Cultures

Illustrative of cell cultures useful for the production of GDPFPP are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, W138, BHK, Cos-7 or MDCK cell lines.

As indicated above, the vector, e. g., a plasmid, which is used to transform the host cell, preferably contains DNA sequences to initiate transcription and sequences to control the translation of the gene sequence. These sequences are referred to as expression control sequences. When the host cell is of insect or mammalian origin illustrative expression control sequences are obtained from the SV-40 promoter (*Science*, 25 222:524–527, 1983), the CMV I.E. Promoter (*Proc. Natl. Acad. Sci.* 81:659–663, 1984) or the metallothionein promoter (*Nature* 296:39–42, 1982). The cloning vector containing the expression control sequences is cleaved using restriction enzymes and adjusted in size as necessary or desirable and ligated with DNA coding for desired polypeptides by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., 1983, *J. Virol.* 45: 773–781).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in DNA Cloning Vol. II a Practical Approach Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. Biochemical Methods in Cell Culture and Virology, Kuchler, R. J., Dowden, Hutchinson and Ross, Inc., (1977). The expressed enzymes are isolated from cells grown as suspensions or as monolayers. The latter are recovered by well known mechanical, chemical or enzymatic means.

D. Preparation of Antibodies to GDPFPP

Methods of producing polyclonal and monoclonal antibodies are known to those of skill in the art. See, e.g., Coligan (1991), CURRENT PROTOCOLS IN IMMUNOLOGY, Wiley/Greene, NY; and Harlow and Lane (1989), ANTIBODIES: A LABORATORY MANUAL, Cold Spring Harbor Press, NY; Stites et al. (eds.) BASIC AND CLINICAL IMMUNOLOGY (4th ed.) Lange Medical Publications, Los Altos, Calif., and references cited therein; Goding (1986), MONOCLONAL ANTIBODIES: PRINCIPLES AND PRACTICE (2d ed.) Academic Press, New York, N.Y.; and Kohler and Milstein (1975), *Nature*, 256:495–497. Such techniques include antibody preparation by selection of antibodies from libraries of recombinant antibodies in phage or similar vectors. See, Huse et al. (1989), *Science*, 246:1275–1281; and Ward et al. (1989) *Nature*, 341:544–546. The antibody can also be selected from a phage display library screened against GDPFPP (see, e.g. Vaughan et al. (1996) *Nature Biotechnology*, 14: 309–314 and references therein). The antibodies or antisera may be used to specifically characterize, detect or isolate proteins that crossreact with SEQ ID NO:2, by any of a variety of methods: Western blotting, immunoaffinity chromatography, ELISA, immunofluorescence microscopy, etc.

For example, in order to produce antisera for use in an immunoassay, the polypeptide of SEQ ID NO: 1 or a fragment thereof is isolated as described herein. For example, recombinant protein is produced in a transformed cell line. An inbred strain of mice or rabbits is immunized with the protein of SEQ ID NO: 2 or a peptide thereof, using a standard adjuvant, such as Freund's adjuvant, and a standard immunization protocol. Alternatively, a synthetic peptide derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-GDPFPP or even GDPFPP from other celltypes or species or a peptide fragment thereof, using a competitive binding immunoassay. Specific monoclonal and polyclonal antibodies and antisera will usually bind with a $K_D$ of at least about 0.1 mM, more usually at least about 1 $\mu$M, preferably at least about 0.1 $\mu$M or better, and most preferably, 0.1 $\mu$M or better.

Specific binding to an antibody under such conditions may require an antibody that is selected for its specificity for a particular protein. For example, antisera raised to a GDPFPP having the amino acid sequence depicted in Seq. ID No. 2 can be selected to obtain antibodies specifically immunoreactive with GDPFPP and not with other proteins.

A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

Immunoassays in the competitive binding format can be used for the crossreactivity determinations. For example, the protein of Seq. ID No. 2 can be immobilized to a solid support. Proteins added to the assay compete with the binding of the antisera to the immobilized antigen. The ability of the above proteins to compete with the binding of the antisera to the immobilized protein is compared to the protein of Seq. ID No. 2. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (i.e., the protein of Seq. ID No. 2). In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein of Seq. ID No. 2 that is required, then the second protein is said to specifically bind to an antibody generated to an immunogen consisting of the protein of Seq. ID No. 2.

This invention also embraces kits for detecting the presence of @ in tissue or blood samples which comprise a container containing antibodies selectively immunoreactive to the protein and instructional material for performing the test. The kit may also contain other components such as @, controls, buffer solutions, and secondary antibodies. Kits for detecting antibodies to @ comprise a container containing an @ instructional material and may comprise other materials such as secondary antibodies and labels as described herein.

E. Methods for Isolating and Purifying GDPFPP

The enzymes of the invention can be directly prepared from cells or tissue in which the enzymes are naturally expressed, or from genetically engineered cells in which they are expressed.

Any of the organisms suitable for isolation of the nucleic acids of the invention can be used as source material for the enzyme. In the case of mammals, the protocol for isolation of the enzymes is generally as follows:

1. Obtain GDPFPP-expressing tissue.
2. Homogenize (e.g., by sonication, or in a dounce homogenizer, or in a blender) in about 1–10 mls of homogenizing solution (containing protease inhibitors, preferably at about 4° C.) per gram tissue.
3. Remove insoluble and particulate matter, by filtration and/or centrifugation.
4. The polypeptides of this invention may be purified to substantial purity by standard techniques well known in the art, including: selective precipitation in a solution in which the GDPFPP is relatively insoluble (e.g., ammonium sulfate, PEG); immunoaffinity chromatography using antibodies to a known GDPFPP such as SEQ ID NO:2; ion exchange chromatography on a commercially available or known ion exchange matrix (for example, DEAE DE-52); hydrophobic chromatography on a commercially available or known matrix (for example, Phenyl Sepharose); gel filtration on a commercially available or known sieving matrix (for example, S-300); dye-ligand chromatography (for example, using Yellow Sepharose and Red Sepharose); chromatofocusing (for example, using PBE 94). See, for instance, R. Scopes, PROTEIN PURIFICATION: PRINCIPLES AND PRACTICE, Springer-Verlag: New York (1982).

The presence, amount and relative activity of GDPFPP in a given sample, especially following a given purification step, is monitored by performing a GDPFPP assay and a protein assay of an aliquot (e.g., 1–1,000 μl) from the sample, as described herein. It is also monitored by sodium dodecyl sulfate polyacrylamide chromatography (SDS-PAGE). The optimal combination and order of purification steps may vary from tissue to tissue and from tissue donor species to species. Using the following example as a basic framework for a purification and analytical scheme, a skilled routineer is capable of determining the better combination and order of purification steps for a given tissue and tissue donor species.

GDPFPP produced by recombinant DNA technology may also be isolated and purified by standard techniques well known to those of skill in the art. Recombinantly produced polypeptides can be directly expressed or expressed as a fusion protein. The protein is then purified by a combination of cell lysis (e. g., sonication) and affinity chromatography. For fusion products, subsequent digestion of the fusion protein with an appropriate proteolytic enzyme release the desired enzyme, which can be purified as described above.

EXAMPLES

Example 1

Purification of GDPFPP from Porcine Kidney

1. Purification of Enzyme

All purification steps were carried out at 4° C. All concentration steps were carried out with an Amicon concentrator with a Diaflo membrane, 10,000 molecular weight (MW) cut-off. A typical isolation protocol is described in detail below.

Homogenization and Centrifugation

One fresh porcine kidney (130 g) was chopped and weighed. Buffer A (10 mM Tris-HCl, pH 7.8. 1 mM ethylenediamine-tetraacetic acid [EDTA], 1 mM β-mercaptoethanol [βME], 50 mM sucrose), was added at 2.5 ml per gram tissue and the tissue was homogenized in a blender for four 1 min. bursts. The sample was centrifuged for 40 min at 12,000×g in a Beckman J-21 centrifuge. The supernatant fraction was filtered through cheesecloth and ultracentrifuged at 100,000×g, for 45 min.

Ammonium Sulfate Precipitation

A 0–30% ammonium sulfate cut was performed on the above supernatant fraction and the sample centrifuged for 40 min at 12,000×g in a Beckman J-21 centrifuge. A 30–60% ammonium sulfate cut was then performed, and after centrifugation as before, the pellet was collected. It was resuspended in and dialyzed against buffer A.

PEG Precipitation

To each 100 ml of dialyzed, resuspended ammonium sulfate pellet, 25 g PEG 8000 were added. The sample was centrifuged at 12,000×g as above, the supernatant fraction discarded, and the pellet resuspended in buffer A.

Ion Exchange Chromatography on DEAE DE-52

A 3 cm×30 cm DE-52 column was equilibrated in buffer A. After loading the sample the column was washed with the same buffer. The enzyme was eluted with a 0–200 mM NaCl gradient in buffer A. Active fractions were pooled.

Hydrophobic Chromatography on Phenyl Sepharose

Phenyl Sepharose (about 100 ml) was equilibrated in buffer A containing 1M ammonium sulfate. Ammonium sulfate was also added to 1M to the enzyme sample. After loading the sample, the column was washed with equilibration buffer. The enzyme was eluted from the column with a 1.0–0 M ammonium sulfate gradient. Active fractions were pooled.

Gel Filtration on S-300

A 1.6×120 cm column of S-300 was equilibrated with buffer A. The enzyme sample was concentrated to 1 ml before loading. Elution was performed with buffer A. Active fractions were pooled.

Dye-Ligand Chromatography on Yellow Sepharose and Red Sepharose

Sigma Reactive Yellow 86 Sepharose (approximately 20 ml) was equilibrated in buffer A. The pooled enzyme from the previous step was applied to the column. The column was washed with buffer A: runthrough and wash fractions, which contained the enzyme, were pooled and concentrated. (The bound contaminants were eluted from the resin with 2 M NaCl and discarded.) Sigma Reactive Red 120 Agarose (approximately 100 ml) was also equilibrated with buffer A. The pooled enzyme that ran through the Yellow Sepharose was loaded and the column washed with buffer A. Some impurities were eluted with 5 mM ATP in buffer A. The enzyme was then eluted with 3 mM pyrophosphate in buffer A.

Gel Filtration on Sephacryl S-300

A 1.6×120 cm column of S-300 was equilibrated with buffer A. The enzyme sample was concentrated to 1 ml before loading. Elution was performed with buffer A.

Chromatofocusing on PBE 94

The PBE 94 column (approximately 20 ml) was equilibrated in 25 mM imidazole-HCl, pH 7.4, 50 mM sucrose, 1 mM EDTA, 1 mM βME. The sample contain enzyme was concentrated to 1 ml and loaded. The column was washed with the equilibration buffer. The column was eluted with a self-forming pH gradient using Polybuffer 74-HCl, pH 4.2, diluted 1:8.

2. Assays for GDPFPP Activity

Three assays for GDP-fucose pyrophosphorylase were used in these studies. Since the reaction is readily reversible, it is possible to assay for the synthesis or hydrolysis of GDP-fucose. Assay #1 measures the pyrophosphate ($PP_i$)-dependent hydrolysis of radiolabeled GDP-fucose. This is the quicker and easier of the two assays and was used to monitor the purification. Assay #2 measures the synthesis of radiolabeled GDP-fucose from radiolabeled GTP and fucose 1-P. This assay is time-consuming but is more specific, and was used to ensure that each completed preparation could indeed be used for the synthesis of GDP-fucose. Only assay #2 was used to screen the cells expressing the cloned enzyme.

Assay #1

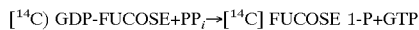

The following reagents are mixed together:
Final Concentration
 100 mM Tris-HCl, pH 7.5
 5 mM sodium pyrophosphate
 4 mM $MgCl_2$
 5000 cpm [$^{14}$C] GDP-fucose
 diluted in 200 mM Tris-HCl,
 pH 7.5
 10 μl enzyme (or enzyme diluted to 10 μl in 200 mM Tris-HCl, pH 7.5), in a reaction volume of 50 μl.
 Incubate 5–10 min, 37° C.
 Add 500 μl 5% (w/v) trichloroacetic acid. Vortex.
 Add 300 μl Darco G-50 (charcoal), 150 mg/ml in water. Vortex 30 sec.
 Centrifuge out charcoal, 1500 rpm, 5 min.
 Count supernatant plus 3 ml scintillation fluid in liquid scintillation counter.

Assay #2

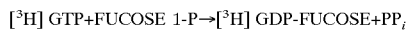

The following reagents are mixed together:

Final Concentration
 $2 \times 10^6 – 1 \times 10^7$ cpm [$^3$H] GTP,
 dried down in SpeedVac
 0.1 mM GTP
 10 mM $MgCl_2$
 50 mU inorganic pyrophosphatase
 10 mM fucose 1-phosphate
 50 mM MOPS or Tris-HCl, pH 7.5
 1 mm GTP
 12.5 mM KF
 (phosphatase inhibitor, optional)
 Enzyme or enzyme plus buffer for balance of volume, total reaction volume 20 μl.
 Incubate 5 min, 37° C.
 Add 10 μl 1 M ammonium sulfate. Mix.
 Add 200 μl ice cold methanol. Mix.
 Microfuge 2 min.
 Count 100 μl supernatant (or a smaller amount if desired) plus 3 ml scintillation fluid in liquid scintillation counter.
 Place remaining supernatant in fresh tube. SpeedVac to dryness.
 Resuspend in 5 μl ethanol. Spot 2 μl on an aluminum-backed silica TLC plate. Use a 1/10 dilution of NEN [$^{14}$C]-GDP-fucose as standard. Dry with low heat.
 Run in 7:3 Ethanol/1 M ammonium acetate pH 7.5, 2–3 hours or till solvent front was at least halfway up the plate. Air dry.
 Spray with En$^3$Hance. Let dry in hood for 10 min. Place in cassette with film (e.g., Kodak XAR film) and an intensifying screen, store at −70° C. for 2 h or overnight if needed.

Preparation of Samples for Assay

When transfected cells were assayed, only assay #2 was used. The cells (from two six well plates) were washed twice with 2 ml/well calcium-magnesium-free PBS and then removed from the plates in the same buffer (2 ml/well) with a cell scraper. The cells were centrifuged in a Beckman GPKR centrifuge, 1500 rpm, for 15 min. The pellet was washed with 2 ml of the PBS and centrifuged as before. Each sample was resuspended in 100 μl of lysis buffer (50 mM Tris-HCl, pH 7.5; 1% (v/v) Triton X100; 10 mM KF; 0.5 mM AEBSF; and 2 μg/ml each antipain, aprotinin, chymostatin, leupeptin and pepstatin). The samples were homogenized with a mini-dounce.

Assay #3

HPLC Assay of GDP-Fucose Pyrophosphorylase (GDPFPP)

A quantitative reverse phase ion pairing HPLC assay for GDPFPP from whole cell lysates has been developed that resolves GDP-fucose from GDP-mannose as well as GTP, GDP, GMP and guanosine. The elution buffers providing the best resolution were 20 mM potassium phosphate (monobasic), 10 mM tetrapropylammonium phosphate, pH 5.0 with $H_3PO_4$ (buffer A) and methanol (buffer B), using a linear gradient of buffer B from 1% to 20% over 20 minutes. Cells expressing recombinant GDPFPP were lysed with nonionic detergent and assayed in the presence of 50 mM Tris, pH 7.5; 10 mM magnesium chloride; 10 mM [$^3$H]GTP; 10 mM fucose-1-phosphate and 10 mUnits of pyrophosphatase for five minutes at 37° C. Assays were quenched with methanol, pelleted, the supernatant was dried under vacuum and resuspended in water for analysis by reverse phase ion pairing HPLC. The formation of GDP-fucose was followed by absorbance and fractions were collected for scintillation counting. Since the specific activity of [$^3$H]GTP in each assay is known, the CPM corresponding to GDP-fucose eluting off the HPLC column can be quantitated. Using this assay, 1 ml of recombinant baculovirus GDPFPP yielded 35 mUnits where a unit is defined as 1 µmole of GDP-fucose formed per minute. Although linearity of this assay has yet to be established, under the conditions utilized, less than 10% of the GTP provided to the cell lysate was consumed, indicating that the assay is in the linear range.

3. Photolabeling $N_3$-[$^{32}$P]-GDP-fucose was synthesized as described for $N_3$-[$^{32}$P]-GDP-mannose in Szumilo, et al., *J. Biol. Chem.*, 268, 17943–17950 (1993), except that partially purified GDPFPP and fucose 1-P were used. The photolabeling experiments were carried out essentially as described in Szumilo, et al., *J. Biol. Chem.*, 268, 17943–17950 (1993) and Potter, et al., *Meth. Enzymol.*, 91, 613–633 (1983).

Highly purified enzyme (10 µl) was incubated with approximately 100 µM $N_3$-[$^{32}$P]-GDP-fucose at room temperature and exposed to short-wave UV radiation via a hand-held UV lamp at a distance of 1.5 cm for 1 min. Novex SDS-PAGE sample buffer containing 1% BME was added to the samples and they were subjected to electrophoresis on 8% or 8–16% gradient gels. Autoradiography was performed on dried gels.

Using the above tyechniques, a 66,000 MW protein that correlated with GDPFPP activity and photolabeled with $N_3$[$^{32}$P]-GDP-fucose was identified.

4. Blotting, Proteolysis and Sequencing

Preparation of Enzyme for Sequencing

After chromatofocusing, the pooled enzyme sample (fractions 18–22, 18 ml) was concentrated to 350 µl with an Amicon concentrator, with a Diaflo membrane. A 200 µl aliquot of that material was concentrated by lyophilization and resuspended in 50 µl DI water.

Blotting

To 40 µl of the lyophilized, resuspended sample, 40 µl Novex SDS-PAGE sample buffer was added, along with 10 mM each DTT and mercaptoacetic acid. The mixture was heated at 100° C. for 5 min. The sample was subjected to electrophoresis in a Novex 8% gel with 10 mm mercaptoacetic acid in the top chamber of the gel box. After electrophoresis, the gel was equilibrated in 10 mm CAPS, pH II.0 with 10% methanol for 15 min. The proteins were blotted onto ABI PVDF (ProBlott) for 1.5 h at 20 V. The blot was washed with water, stained with 0.2% Ponceau S in 1% acetic acid destained in 1% acetic acid and washed with water. The appropriate protein was excised from the blot, placed in a 1.5 ml centrifuge tube, washed with water, and kept moist. The sample was stored at −20° C. until shipping.

Proteolysis and Sequencing

The isolated protein was subjected to in situ proteolysis with trypsin. Before pooling and proteolysis, 10% of each sample was subjected to amino acid analysis. Peptides were separated on a Vydac C-18 column. Strong, symmetrical peaks were chosen for sequence analysis.

Example 2

PCR Amplification, Isolation and Cloning of cDNAs Coding for the Enzyme

Using the amino acid sequences of portions of the porcine protein, human nucleic acid sequences comprising sequences that could encode these partial amino acid sequences were identified in computer databases comprising expressed sequence tags (ESTs). A full-length cDNA was then obtained by polymerase chain reaction using the following primers and amplification conditions.

The first human EST that matched with a porcine GDPFPP peptide sequence was GenBank accession #T75166 (NCBI gi: 691928). This EST is from the Merck-Washington University sequencing project and is 465 basepairs long, 335 bp of which was considered high quality sequence. A shorter identical EST sequence was also identified in the search, accession #F12805 from Genethon's cDNA sequencing project. Another two ESTs (not shown) were discovered after large sequences of the gene had been isolated and sequenced.

The full-length cDNA was cloned into an appropriate vector and expressed in COS cells as follows.

1. Source of DNA Template for PCR Amplification

A cDNA library was made from the an Epstein-Barr-virus-transformed B lymphoblastoid cell line, JY (Terhost, C., et al., *Proc. Natl. Acad. Sci. USA* 73:910), into the plasmid DNA vector pBSIISK(+)(Stratagene) following the protocols for RNA isolation, mRNA purification and cDNA library construction found in GENE TRANSFER AND EXPRESSION: A LABORATORY MANUAL, M. Kriegler, W. H. Freeman and Company (1990). A 0.1 ml aliquot of the library glycerol stock was inoculated into 500 ml LB growth media, supplemented with ampicillin at 50 µg/ml, and grown at 37° C. for 16 hours with agitation. The library DNA was isolated using the Qiagen Plasmid Isolation Kit following conditions provided by the vendor.

2. PCR Amplification

The human GDPFPP cDNA was amplified from the JY-cDNA library using native Pfu polymerase (Stratagene) and the polymerase chain reaction (PCR) using Buffer #1 and conditions supplied by the manufacturer. The primers generate Eco RV restriction sites at the 5' and 3' termini. The 5' and 3' primers were 5'-TCA-GAT-ATC-GGG-GCT-ATG-GCA-GCT-GCT-AG-3' (SEQ ID NO: 4) and 5'-ATA-GAT-ATC-TCT-GGA-ATG-TTA-CTC-AAA-AAG-GCA-A-3' (SEQ ID NO: 5), respectively. The PCR procedure amplified a 1.8 kb fragment.

3. Cloning the GDPFPP cDNA into Expression Vectors

The amplified GDPFPP gene was digested with the enzyme Eco RV (New England Biolabs) using conditions provided by the manufacturer. The blunt-end 1.8 kb fragment was fractionated on an agarose gel and isolated using standard techniques. The 1.8 kb fragment was cloned into the Eco RV site of pcDNA3 (Invitrogen), the Sma I site of pEE12 (Celltech), and the Sma I site of pVL-1392 (Invitrogen) following standard techniques, generating pcDNA-GFP6, pEE12-GFP7, and pVL1392-GFP6, respectively.

4. Transient Expression of GDPFPP in COS Cells

COS cells were transfected via deae-dextran with either plasmid pcDNA3 or plasmid pcDNA-GFP6 following the protocol in GENE TRANSFER AND EXPRESSION: A LABORATORY MANUAL, M. Kriegler. After a 72 hour incubation, cell lysates were assayed for GDPFPP activity by the TLC-GDPFPP assay. Cells transfected with pcDNA-GFP6 generated GDP-fucose from fucose-1-phosphate and GTP.

5. Stable Expression of GDPFPP in NSO Cells

NSO cells were transfected by electroporation with plasmid pEE12-GFP7 and glutamine synthetase positive clones were isolated following the procedures in [PATENT: NSO-GT]. Clones were screened for GDPFPP activity by the TLC-GDPFPP assay. Clone GFP-5 was assayed via the HPLC-GDPFPP to produce 1.9 nanounits GDPFPP/cell.

6. Construction of GDPFPP-recombinant Baculovirus and GDPFPP Expression

Stock cultures of *Spodoptera frugiperda* insect cells (Sf9II; Gibco/BRL) were co-transfected with pVL1392-GFP6 and linearized BaculoGold viral DNA (PharMingen) using the transfection protocol of Invitrogen Inc. Recombinant GDPFPP-baculoviruses were isolated and a high-titer stock generated by standard techniques. Sf9II cells were infected at a multiplicity of infection of 3. Following a 72-hour incubation at 27° C. the cells were harvested and GDPFPP purified. GDPFPP was assayed via the HPLC-GDPFPP to produce 5.8 nanounits GDPFPP/cell.

Example 3

Assay of the Transfected Cells

Lysates of COS cells transiently transfected with vector alone or with vector containing the full length cDNA clone were assayed for GDPFPP activity using Assay #2 described in Example 1. Each sample was assayed with either fucose 1-phosphate or an inappropriate sugar phosphate, glucose 1-phosphate. Specific GDPFPP activity was observed in the COS cells expressing the cDNA. In particular, GDP-fucose was detected in assay products of lysates from the cells transfected with the GDPFPP clone, but not in the vector alone condition. Additionally, a significant quantity of nucleotide sugar was not synthesized when glucose 1-phosphate was offered as a substrate.

Example 4

Recombinant GDPFPP from Baculovirus-infected Sf9 Cells Can Be Used in the Fucosyltransferase Cycle for the Production of Cylexin™

Cylexin™ is the brand name for a pentasaccharide that inhibits the adhesion of cells that express NeuAcα2→3Galβ1→4(Fucα1→3)GlcNAc (SLe$^x$) to selectin receptors such as ELAM-1. Recombinant GDPFPP from baculovirus-infected Sf9 cells can be used in the fucosyltransferase cycle for the production of Cylexin™.

1. Synthesis of GFP in Baculovirus Cultures

Sf-9 cells were grown and passaged in Sf-900 II medium (GIBCO-BRL) in 50 ml shaker flask culture, under conditions recommended by the media manufacturer. The cells were grown at 27 C in the dark with continuous shaking at 130 rpm. To create a recombinant virus, standard protocols were used (see O'Reilly D R, Miller L K, and Luckow V (1992), BACULOVIRUS EXPRESSION VECTORS: A LABORATORY MANUAL. New York; W. H. Freeman Co.) with some modifications. Cells were co-transfected with *Baculogold baculovirus* DNA [Pharmingen, San Diego, Calif.] and the purified transfer vector, according to the Baculogold manufacturers directions. Transfected cells were incubated in Sf-900 II medium for five days after transfection, when the supernatant was collected. Recombinant virus was isolated by limiting dilution on fresh Sf-9 cells in 60-well tissue culture dishes [Robbins Scientific].

After 7 days, virus was collected from wells containing infected cells at dilutions that yielded less than 20% infected wells. Twelve recombinant viruses were expanded in volume by infection of fresh cells in 24-well tissue culture dishes. After 7 days, each virus isolate was screened for its ability to synthesize GFP, and each isolate was found to be positive. One isolate (designated E-9) was chosen for further expansion by infection of fresh Sf-9 cells in a 225 cm$^2$ flask. The virus stock produced after 7 days of infection was collected and stored as virus master stock, designated rBacv GFP p3.

Sf-9 cells were grown to 1000 ml shake flask culture in a 2800-ml Fernbach flask in suspension culture at 27 C, 130 rpm until the culture reached a density of 8×10$^6$ cells per ml of culture. Virus titre of the master stock was assumed to be 3×10$^8$ pfu/ml, and the Sf-9 cells were infected at a multiplicity of infection of approximately 0.2 pfu/cell in the following manner: 5 ml of virus stock were added to the cells in the Fernbach flask. The flask was swirled by hand 4–5 revolutions to distribute the virus. 500 ml of fresh media were added, and the flask was returned to the shaking incubator for 48 hours. After incubation, the virus was collected aseptically in the supernatant. The culture was transferred to sterilized one-liter bottles and the cells were centrifuged away (3,000×g, 15 min) from the supernatant (virus working stock), which was collected and stored. The titre of the virus working stock was determined by calculation from the results of limiting dilution infection, as described in O'Reilly et al., and was determined to be 2.4×10$^9$ pfu/ml.

To produce GFP, Sf-9 cells were grown to 1000 ml shake flask culture in three 2800-ml Fernbach flasks in suspension culture at 27 C, 130 rpm until the cultures reached a density of approximately 8×10$^6$ cells per ml of culture. The cells were infected at a multiplicity of infection of approximately 3 pfu/cell using the method described above, with the modification of addition of 10 ml of virus working stock to each flask to achieve the desired multiplicity. After addition of virus, 500 ml of fresh media was added to each flask, and the cultures were returned to the shaking incubator for 65 hours. A one-ml analytical sample was collected and centrifuged (5000×g, 2 min), and the cells and supernatant were analyzed for GFP content. The remaining cells were harvested by centrifugation in one-liter bottles (3,000×g, 25 min), resuspended in a small amount of fresh medium, combined, and recentrifuged. Supernatants were discarded.

2. Partial Purification of GDPFPP from Baculovirus-infected Sf9 Cells

A 75×g cell pellet was obtained from centrifugation of a 4 L culture of Sf9 cells infected with baculovirus harboring the cDNA for GDPFPP. The pellet was resuspended in 50 Mm Tris-HCl, pH 7.8 plus 2 μg/ml each antipain, aprotinin, chymostatin, leupeptin and pepstatin. The sample was sonicated with a Tekmar Sonic Disruptor at 60% power for 6–15 sec. bursts. The sample was centrifuged at 4° C. in a Sorvall RC-5B centrifuge in a GSA rotor at 8000 rpm for 30 min. The pellet was discarded. While the supernatant fraction was stirring rapidly, 3.5 ml of a 10% (v/v) solution of polyethylen(imine) was added. The mixture was centrifuged at 4° C. in a Sorvall RC-5B centrifuge in a GSA rotor at 8000 rpm for 15 min. The pellet was discarded. Solid ammonium sulfate was added to 60% saturation and the sample stirred at 40 C for 1 hour. The mixture was centrifuged at 4° C. in a Sorvall RC-5B centrifuge in a GSA rotor at 8000 rpm for 15 min. The supernatant fraction was discarded. The pellet was resuspended in 20 ml 50 mM Tris-HCl, pH 7.8.

3. The Fucosyltransferase Cycle

A fucosyltransferase cycle was run in a volume of 100 μl with the following reagents: 50 mM sialy-N- acetyllactosamine; 50 mM HEPES, pH 7.5; 100 mM phosph (enol)pyruvate, adjusted to pH 7.5; 2 mM guanosine 5'-diphosphate; 0.7 U pyruvate kinase; 50 mM fucose 1-phosphate; 5 mM MgCl$_2$; 0.5 mg/ml (w/v) bovine serum albumin; 0.2% (w/v) NaN$_3$; 15% (v/v) GDPFPP purified as described above; and 15% (v/v) fucosyltransferase V (α-1,3 fucosyltransferase, 2.16 U/ml, partially purified on SP-Sepharose). The cycle was incubated at 37° C. overnight. A 0.3 μl aliquot of a 10 mM solution was clearly apparent in the lane containing the fucosyltransferase cycle sample. A 0.3 μl sample of the cycle spiked with 0.3 μl of a 3.3 mM solution of Cylexin™ standard was run on the same plate to confirm the identity of the cycle product as Cylexin™.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A composition comprising an isolated GDP-fucose pyrophosphorylase (GDPFPP) enzyme encoded by a nucleic acid which hybridizes to SEQ ID NO: 1 under hybridization conditions that include washing in 6×SSC at a temperature of at least about 42° C.

2. The composition of claim 1, wherein the isolated GDPFPP enzyme is as shown in SEQ ID NO:2.

3. The composition of claim 1, wherein the nucleic acid is as shown in SEQ ID NO:1.

4. The composition of claim 1, further comprising a fucosyltransferase.

5. The composition of claim 4, where in the fucosyltransferase is fucosyltransferase V.

6. The composition of claim 4, further comprising an oligosaccharide substrate for the fucosyltransferase.

7. The composition of claim 6, wherein the oligosaccharide comprises a sialyl residue.

8. The composition of claim 1, further comprising a compound comprising the sialyl Lewis$^x$ ligand.

9. The composition of claim 1, wherein the GDPFF enzyme is partially purified from Sf9 cells.

10. The composition of claim 1, wherein the GDPFF enzyme is in a transgenic cell.

\* \* \* \* \*